(12) United States Patent
Kochelek et al.

(10) Patent No.: US 9,839,802 B2
(45) Date of Patent: *Dec. 12, 2017

(54) CORROSION MONITORING IN A FIRE SPRINKLER SYSTEM

(71) Applicant: Engineered Corrosion Solutions, LLC, St. Louis, MO (US)

(72) Inventors: Jeffrey T. Kochelek, Creve Coeur, MO (US); Adam H. Hilton, Chesterfield, MO (US); Lucas E. Kirn, St. Louis, MO (US)

(73) Assignee: Engineered Corrosion Solutions, LLC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,771

(22) Filed: Jun. 24, 2015

(65) Prior Publication Data

US 2015/0290483 A1 Oct. 15, 2015

Related U.S. Application Data

(63) Continuation of application No. 14/304,655, filed on Jun. 13, 2014, now Pat. No. 9,095,736, which is a (Continued)

(51) Int. Cl.
*G01M 3/28* (2006.01)
*A62C 37/50* (2006.01)
(Continued)

(52) U.S. Cl.
CPC .............. *A62C 37/50* (2013.01); *A62C 35/60* (2013.01); *A62C 35/62* (2013.01); *A62C 35/68* (2013.01);
(Continued)

(58) Field of Classification Search
CPC .......... G01N 17/00; G01M 3/04; G01M 3/18; G01M 3/22; G01M 3/243; G01M 3/2815;
(Continued)

(56) References Cited

U.S. PATENT DOCUMENTS 442,385 A 12/1890 Neu
3,490,271 A 1/1970 Hays
(Continued)

FOREIGN PATENT DOCUMENTS

FR 2299916 A1 9/1976
JP 200254800 2/2002
(Continued)

*Primary Examiner* — Alexander Valvis
(74) *Attorney, Agent, or Firm* — Harness, Dickey & Pierce, P.L.C.

(57) ABSTRACT

A fire sprinkler system according to one aspect of the present disclosure includes a pipe having a first pipe portion and a second pipe portion. The first pipe portion includes a wall having a first wall thickness, and the second pipe portion includes a wall having a second wall thickness that is greater than the first wall thickness. The fire sprinkler system further includes structure coupled to the pipe and defining a sealed chamber between the structure and at least the first pipe portion, and a sensor for sensing a pressure in the sealed chamber. Example corrosion monitoring devices and methods for monitoring corrosion in pipe systems, including fire sprinkler systems, are also disclosed.

22 Claims, 8 Drawing Sheets

Related U.S. Application Data continuation of application No. PCT/US2014/037144, filed on May 7, 2014.

(60) Provisional application No. 61/833,572, filed on Jun. 11, 2013, provisional application No. 61/820,439, filed on May 7, 2013.

(51) Int. Cl.

| | | |
|---|---|---|
| *A62C 35/68* | (2006.01) | |
| *G01M 3/22* | (2006.01) | |
| *F16L 55/16* | (2006.01) | |
| *G01M 3/18* | (2006.01) | |
| *F16L 55/168* | (2006.01) | |
| *A62C 35/60* | (2006.01) | |
| *A62C 35/62* | (2006.01) | |
| *G01N 17/00* | (2006.01) | |

(52) U.S. Cl.
CPC ............. *F16L 55/16* (2013.01); *F16L 55/168* (2013.01); *F16L 55/1683* (2013.01); *G01M 3/18* (2013.01); *G01M 3/223* (2013.01); *G01M 3/283* (2013.01); *G01M 3/2853* (2013.01); *G01N 17/00* (2013.01); *F16L 2201/30* (2013.01); *Y10T 29/49815* (2015.01)

(58) Field of Classification Search
CPC .... G01M 3/283; G01M 3/223; G01M 3/2853; F16L 2201/30; F16L 9/18; F16L 55/16; F16L 55/168; F16L 55/1683
USPC .............................................. 73/40–49.8, 86
See application file for complete search history.

(56) References Cited

U.S. PATENT DOCUMENTS

| | | |
|---|---|---|
| 3,942,546 A | 3/1976 | Radd et al. |
| 4,002,295 A | 1/1977 | Drori |
| 4,389,877 A | 6/1983 | Lacey |
| 4,575,678 A | 3/1986 | Hladky |
| 4,644,780 A | 2/1987 | Jeter |
| 4,683,035 A | 7/1987 | Hunt et al. |
| 4,683,917 A | 8/1987 | Bartholomew |
| 4,939,923 A | 7/1990 | Sharp |
| 4,945,758 A | 8/1990 | Carpenter |
| 5,171,524 A | 12/1992 | Niolon |
| 5,209,105 A | 5/1993 | Hasha et al. |
| 5,450,765 A | 9/1995 | Stover |
| 6,277,329 B1 | 8/2001 | Evans |
| 6,758,282 B2 * | 7/2004 | Pliner .................... A01N 33/12 118/306 |
| 7,681,435 B2 | 3/2010 | Schippl et al. |
| 7,836,966 B2 | 11/2010 | McHugh et al. |
| 8,470,423 B2 | 6/2013 | Jarvenkyla |
| 8,701,467 B2 | 4/2014 | Carns et al. |
| 2002/0033042 A1 | 3/2002 | Brooker et al. |
| 2004/0231862 A1 | 11/2004 | Kirn et al. |
| 2005/0166666 A1 | 8/2005 | Tsukagoshi |
| 2009/0068060 A1 | 3/2009 | Alfermann et al. |
| 2012/0031629 A1 | 2/2012 | Kochelek et al. |
| 2012/0168538 A1 | 7/2012 | Han |

FOREIGN PATENT DOCUMENTS

| | | |
|---|---|---|
| JP | 2002340236 | 11/2002 |
| JP | 2002349800 | 12/2002 |

* cited by examiner

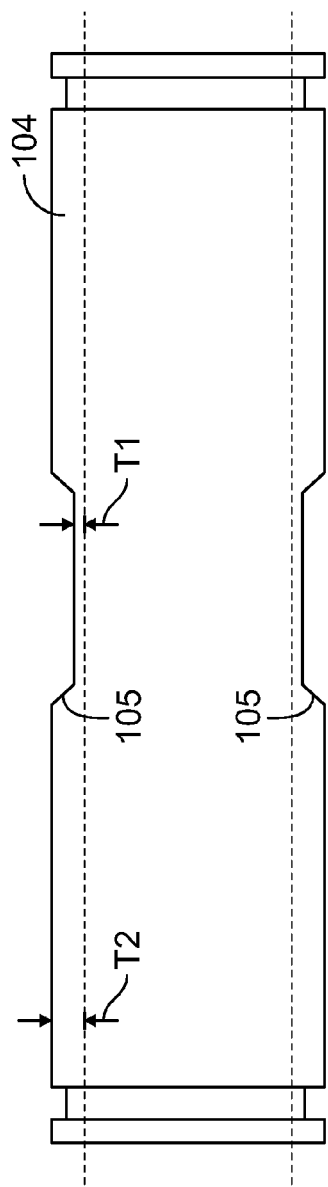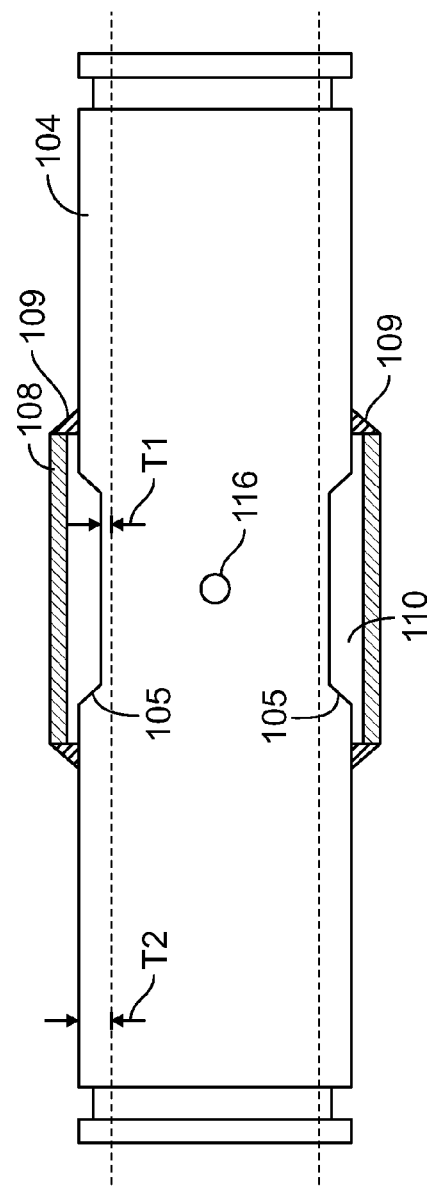

CORROSION MONITORING IN A FIRE SPRINKLER SYSTEM

CROSS-REFERENCE TO RELATED APPLICATIONS

This application is a continuation of U.S. application Ser. No. 14/304,655 filed Jun. 13, 2014, which is a continuation of International Application No. PCT/US14/37144 filed May 7, 2014, which claims the benefit of U.S. Provisional Application No. 61/820,439 filed May 7, 2013, and U.S. Provisional Application No. 61/833,572 filed Jun. 11, 2013. The entire disclosures of the above applications are incorporated herein by reference.

FIELD

The present disclosure relates to devices and methods for monitoring corrosion in pipe systems, including fire sprinkler systems.

BACKGROUND

This section provides background information related to the present disclosure which is not necessarily prior art.

Water-based fire sprinkler systems are commonly used to protect buildings, property and people from fire. There are two main types of water-based fire sprinkler systems: wet pipe sprinkler systems and dry pipe sprinkler systems.

In wet pipe sprinkler systems, the piping network remains filled with water until the system is actuated. If exposed to freezing temperatures, the water in the piping network may freeze and cause the piping network to burst, resulting in substantial property damage and rendering the system inoperable. Therefore, wet pipe sprinkler systems are not well suited for applications involving freezing temperatures.

Dry pipe sprinkler systems can be used to protect unheated structures and other areas where the system is subject to freezing temperatures. Dry pipe systems (including preaction systems) are also used in locations where accidental water discharge from the system would be highly undesirable, such as museums, libraries and computer data centers. In dry pipe sprinkler systems, the piping network is filled with a pressurized gas (rather than water) until the system is actuated.

DRAWINGS

The drawings described herein are for illustrative purposes only of selected embodiments and not all possible implementations, and are not intended to limit the scope of the present disclosure.

FIG. 2 is a side view of a pipe, a portion of which has a reduced wall thickness according to another example embodiment.

FIG. 3 is a side view of the pipe of FIG. 2 with a sleeve centered over the reduced wall thickness portion.

Corresponding reference numerals indicate corresponding parts throughout the several views of the drawings.

SUMMARY

Figure 1:
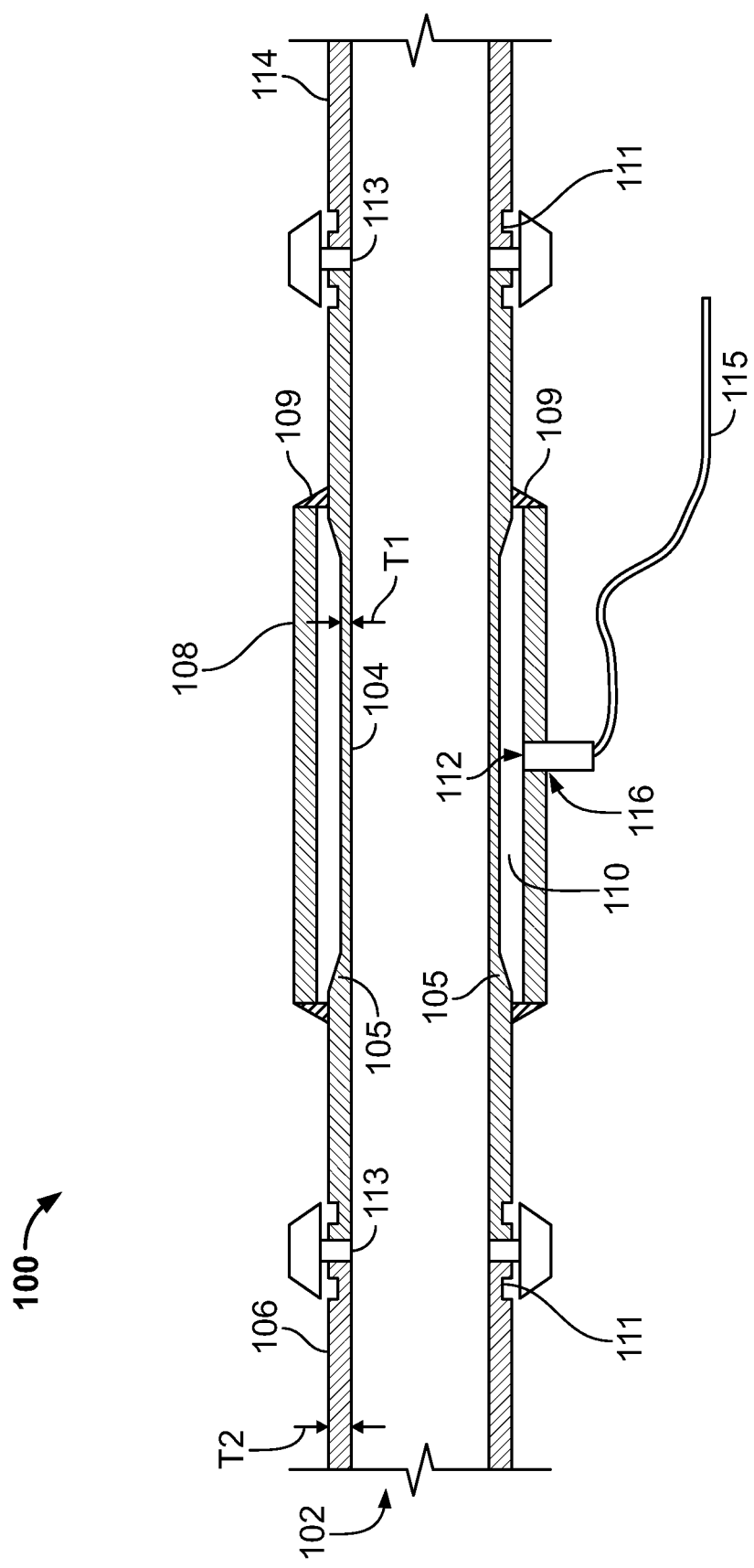
FIG. 1 is a side cross-sectional view of a corrosion monitoring assembly in a fire sprinkler system according to one example embodiment of the present disclosure.

This section provides a general summary of the disclosure, and is not a comprehensive disclosure of its full scope or all of its features.

According to one aspect of the present disclosure, a fire sprinkler system includes a pipe having a first pipe portion and a second pipe portion. The first pipe portion includes a wall having a first wall thickness, and the second pipe portion includes a wall having a second wall thickness that is greater than the first wall thickness. The fire sprinkler system further includes structure coupled to the pipe and defining a sealed chamber between the structure and the first pipe portion, and a sensor for sensing a pressure in the sealed chamber.

According to another aspect of the present disclosure, a corrosion monitoring device for a fire sprinkler system includes a pipe having opposite ends and a middle portion positioned between the opposite ends. The opposite ends of the pipe each include a wall having a first wall thickness, and the middle portion of the pipe includes a wall having a second wall thickness that is less than the first wall thickness. The corrosion monitoring device further includes structure coupled to the pipe and defining a sealed chamber between the structure and the pipe, and a sensor for sensing a pressure in the sealed chamber.

According to yet another aspect of the present disclosure, a method of installing a corrosion monitoring device in a fire sprinkler system having a pipe is disclosed. The method includes removing a section of the pipe from the fire sprinkler system to create two pipe ends with a space between, positioning the corrosion monitoring device in the space, and coupling the corrosion monitoring device to the two pipe ends.

According to another aspect of the present disclosure, a fire sprinkler system includes a pipe having a first pipe portion and a second pipe portion. The first pipe portion includes a wall having a first wall thickness, and the second pipe portion includes a wall having a second wall thickness. The fire sprinkler system also includes structure coupled to the pipe and defining a sealed chamber between the structure and the first pipe portion, and a sensor for sensing a parameter associated with the sealed chamber.

According to yet another aspect of the present disclosure, a corrosion monitoring device for a fire sprinkler system includes a pipe having opposite ends and a middle portion positioned between the opposite ends. The opposite ends of the pipe each include a wall having a first wall thickness, and the middle portion of the pipe includes a wall having a second wall thickness. The corrosion monitoring device further includes structure coupled to the pipe and defining a sealed chamber between the structure and the first pipe portion, and a sensor for sensing a parameter associated with the sealed chamber.

According to another aspect of the present disclosure, a method of monitoring corrosion within a fire sprinkler system having a pipe, and structure coupled to the pipe and defining a sealed chamber between the structure and the pipe, is disclosed. The method includes sensing, with a pressure sensor, a pressure within the sealed chamber. The method also includes detecting a change in pressure within the sealed chamber, corresponding to a breach of a pipe wall of the sealed chamber. The method further includes generating a signal in response to detecting the change in pressure within the sealed chamber.

According to yet another aspect of the present disclosure, a method of monitoring corrosion within a fire sprinkler system having a pipe, and structure coupled to the pipe and defining a sealed chamber between the structure and the pipe, is disclosed. The method includes sensing a parameter associated with the sealed chamber, and detecting a change in the parameter associated with the sealed chamber, corresponding to a breach of a pipe wall of the sealed chamber. The method also includes generating a signal in response to detecting the change in the parameter associated with the sealed chamber.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

DETAILED DESCRIPTION

One example embodiment of a fire sprinkler system according to the present disclosure is illustrated in FIG. 1 and indicated generally by reference number 100. As shown in FIG. 1, the fire sprinkler system 100 includes a pipe 102 including a first pipe portion 104 and a second pipe portion 106. The first pipe portion 104 includes a wall having a first wall thickness T1, and the second pipe portion 106 includes a wall having a second wall thickness T2 that is greater than the first wall thickness T1. The fire sprinkler system 100 further comprises structure 108 coupled to the pipe 102 and defining a sealed chamber 110 between the structure 108 and the first pipe portion 104. The system 100 also includes a sensor for sensing a pressure in the sealed chamber 110.

Because the first pipe portion 104 includes a wall with a lesser wall thickness T1 as compared to the second pipe portion (and optionally any other pipe portion in the fire sprinkler system), any breach through a pipe wall in the fire sprinkler system due to corrosion should occur first in the first pipe portion 104. Such a breach will cause a pressure change in the sealed chamber 110 and can be detected by the sensor. In that event, corrective action can be taken before the overall system 100 is breached and allows water to escape, which would potentially (or likely) result in expensive damage, business interruption, etc.

The first pipe portion 104 may have the same material composition as the second pipe portion 106 (and/or the third pipe portion discussed below) so various pipe portions are equally subject to corrosion (i.e., if subjected to the same environmental conditions). The pipe portions may comprise black steel, galvanized steel, stainless steel, copper and/or other suitable material(s).

The first pipe portion 104 and the second pipe portion 106 (and the third pipe portion) may have the same inner diameter, and preferably have or contain no obstructions that could impede the flow of water therethrough.

Optionally, the first pipe portion 104 may be substantially identical to the second pipe portion 106 (and the third pipe portion) in every respect, except for the lesser wall thickness T1 of the first pipe portion 104. For example, the pipe portions may have the same material composition, the same inner diameter, the same interior surface texture, the same galvanized layer (if applicable), the same weld seam (if applicable) positioned in the same orientation (i.e., the same "clocking"), etc. As a result, the interior surface of the first pipe portion 104 may experience the same corrosion process as the second pipe portion 106 (and the third pipe portion), and may therefore constitute an accurate gauge of any corrosion damage in the second pipe portion 106, the third pipe portion and/or other pipe portions in the fire sprinkler system 100.

The wall thickness of the second pipe portion 106 (i.e., thickness T2) may gradually lessen to the thickness of the first pipe portion 104 (i.e., thickness T1) at milled shoulders 105.

In the particular embodiment shown in FIG. 1, the sealed chamber 110 extends around the circumference of the first pipe portion 104. As a result, the entire circumference can be monitored for a breach due to corrosion. Alternatively, the sealed chamber 110 may extend about only a portion of the first pipe portion, preferably including the bottom side of the first pipe portion 104 (i.e., at the six o'clock position) or the top side of the first pipe portion 104 (i.e., at the twelve o'clock position) where a breach due to corrosion may be most likely to occur (which may depend on whether the system 100 is a dry pipe or wet pipe fire sprinkler system). In the particular embodiment shown in FIG. 1, the height of the sealed chamber 110 from the outer surface of the first pipe portion 104 is constant around the circumference of the first pipe portion 104, but in other embodiments the height of the sealed chamber 110 may vary along portions of the pipe.

As shown in FIG. 1, the pipe 102 includes a third pipe portion 114 similar to the second pipe portion 106. The structure 108 is coupled to the first pipe portion 104 via welding (i.e., at weld joints 109) on opposite sides of the wall having the thinner wall thickness T1, and at locations having the same wall thickness T2 as the second and third pipe portions 106, 114. Alternatively, the structure 108 may be coupled to the first pipe portion 104 in another suitable manner (i.e., without welding), at other suitable locations of the first pipe portion 104, and/or may be coupled to the second and/or third pipe portions 106, 114 to define the sealed chamber 110.

As further shown in FIG. 1, the structure 108 may include a sleeve having an inner diameter that is greater than the outer diameter of the first, second and third pipe portions 106, 114. Further, the sleeve may be coaxial with the first pipe portion 104 and have the same cross-sectional shape (i.e., circular). Alternatively, the structure 108 can have various other configurations for forming the sealed chamber 110, and may not include a sleeve.

In the example shown in FIG. 1, the first pipe portion 104, structure 108, sealed chamber 110 and sensor constitute a corrosion monitoring assembly that is coupled to the second and third pipe portions 106, 114 via roll grooved and/or cut grooved couplings 111, which may include gaskets 113. Alternatively, the corrosion monitoring assembly may be coupled to the second and/or third pipe portions via other suitable means, such as threaded couplings, welding, etc.

The first pipe portion may have opposite ends and a middle portion positioned between the opposite ends. The opposite ends of the pipe each may include a wall having a first wall thickness, and the middle portion of the pipe may include a wall having a second wall thickness. The second wall thickness may be less than the first wall thickness. Alternatively, the first and second wall thicknesses may be the same (i.e., no lesser wall thickness).

As another alternative, the first, second and third pipe portions may constitute a single, continuous piece of pipe (having different wall thicknesses along its length), with the corrosion monitoring assembly formed integrally therewith (e.g., when the fire sprinkler system 100 is fabricated and installed), rather than separate pipe sections that are coupled together.

As yet another alternative, the corrosion monitoring assembly may extend along the entire length of the pipe 102. In that event, the assembly may include two or more sealed chambers for detecting breaches due to corrosion in various regions of the pipe 102.

Pipe 102 may include multiple corrosion monitoring assemblies, which may be used to detect corrosion at multiple locations along pipe 102. Alternatively, or in addition, one or more corrosion monitoring assemblies may be provided on other pipes in the system 100 (i.e., in addition to pipe 102).

The corrosion monitoring assembly may have substantially the same pressure rating (i.e., the pressure rating of the first pipe portion 104 of the corrosion monitoring assembly) as one or more pipes in the system 100 (i.e., including pipe 102), or may have a greater or lesser pressure rating. In some example embodiments, the corrosion monitoring assembly may have a pressure rating of about 175 PSIG.

The sensor may be any suitable type of sensor for sensing a pressure in the sealed chamber 110. For example, the sensor may be an electronic pressure transducer, a pneumatic sensor, a pressure switch (e.g., a UL listed and/or FM approved pressure switch for use in fire sprinkler systems), etc. Further, the sensor may be positioned in the sealed chamber 110, or may be coupled to the sealed chamber 110 via a diaphragm, pressure tubing, or other suitable means. In the particular embodiment shown in FIG. 1, the structure 108 includes a sleeve defining the sealed chamber 110, and the sensor includes (i) a pressure tubing connector 112 (e.g., a ¼ inch male national pipe thread taper (MNPT)) coupled to a port 116 (e.g., a ¼ inch female national pipe thread taper (MNPT)) in the sleeve defining the sealed chamber 110, (ii) pressure tubing 115 coupled to the pressure tubing connector 112, and (iii) a pressure switch or transducer (not shown) coupled to the pressure tubing. As should be apparent, however, numerous other sensor configurations may be employed without departing from the teachings of this disclosure. For example, if the system 100 is a wet pipe sprinkler system, the sensor may be configured to detect the presence or absence of a liquid (i.e., instead of or in addition to sensing a pressure) in the sealed chamber, where the detection of a liquid would indicate a breach through the first pipe portion 104.

Additionally, or alternatively, the sensor may be configured to produce an analog and/or digital signal representing a pressure (including a change in pressure) or other parameter in the sealed chamber 110, such as the absence or presence of a liquid, temperature, etc. Further, the sensor may be connected via a wired and/or wireless communication channel to a fire alarm panel, a building management system and/or a corrosion monitoring station (e.g., onsite or offsite), which may generate alarm(s) and/or take other appropriate action(s) in response to detecting a breach through the wall of the first pipe section 104. For example, the sensor may be a pressure switch including a dry contact wired to a monitoring station.

The fire sprinkler system 100 may be of any desired type or configuration, including a wet pipe system and a dry pipe system (including preaction systems). In some embodiments, the fire sprinkler system 100 may be substantially filled with water and/or an inert gas (e.g., nitrogen) to inhibit corrosion in the fire sprinkler system.

A method of making a corrosion monitoring assembly according to another example embodiment is illustrated in FIGS. 2 and 3. In particular, FIG. 2 illustrates a length of what is referred to as "two inch" schedule 40 black steel pipe 104, having an external dimension of about 2.38 inches, an internal dimension of about 2.07 inches, a nominal thickness of about 0.154 inches (154 mils), a length of about twelve inches, and a rolled groove end finish.

FIG. 3 illustrates a length of "2½ inch" schedule 40 black steel pipe 108, having an external dimension of about 2.88 inches, an internal dimension of about 2.47 inches, a nominal thickness of about 0.203 inches (203 mils), a length of about three inches, and a straight cut end finish. As shown in FIG. 2, a portion of the two inch pipe 104 may be milled down (e.g., via a lathe), or otherwise formed, to create an area having a reduced wall thickness T1 (preferably with milled shoulders 105 on both ends of the milled section, as shown in FIGS. 2 and 3). The reduced wall thickness may be about 20-30 mils, and may be about two inches in length, although it should be understood that other reduced wall thicknesses and/or lengths may be used in other embodiments. The 2½ inch pipe 108 constitutes a sleeve that is centered over the reduced wall thickness portion of the two inch pipe 104 and welded in place, preferably to non-"reduced" portions, as shown in FIG. 3 at weld joints 109. Optionally, the assembly may be subjected to heat annealing to eliminate any heat affected zones created by the welding. A tapped port 116 is formed in the sleeve 108 (e.g., tapped in the center of the sleeve 108) for attaching a sensor (not shown), a pressure tubing connector (not shown), etc., to facilitate sensing a pressure and/or other parameter in the sealed chamber 110 formed between the outer sleeve 108 and the inner pipe 104. Optionally, the sealed chamber 110 may be pressure tested to verify its integrity and the absence of any leaks before the assembly is placed into service.

The corrosion monitoring assembly may be installed in a fire sprinkler system at a location most susceptible to corrosion (e.g., where water is likely to collect in a dry pipe system, where air is likely trapped in a wet pipe system, etc.). For example, the fire sprinkler system (or other pipe system) can be analyzed (e.g., using a scope) to identify such locations before installing corrosion monitoring devices at such locations.

To install the corrosion monitoring assembly in a preexisting fire sprinkler system, a section of pipe may be cut and removed from the preexisting system (e.g., from a location most susceptible to corrosion as noted above). For example, if the corrosion monitoring assembly is about eighteen inches in length, an eighteen inch section of pipe may be removed from the preexisting system. The corrosion assembly may be selected based on the characteristics of the pipe in the preexisting system (e.g. the inner pipe has the same schedule, type of steel, inner diameter, etc.). Optionally, the removed section of pipe may be used to fabricate the first pipe portion 104 of a corrosion monitoring assembly. In that event, the existing pipe sections to which the corrosion monitoring assembly will be coupled will have the same characteristics as the first pipe portion 104 (except for the reduced wall thickness of the first pipe portion 104), including any preexisting corrosion damage. The remaining ends of the preexisting system pipe may be roll grooved prior to installation of the corrosion monitoring device to assist in connecting the grooved end type couplings of the corrosion monitoring device. The exterior surface of the assembly may receive a powder coat finish, which may correspond to the powder coat finish of the preexisting system pipe.

The various corrosion monitoring devices described herein may be installed "in situ" within a piping system, meaning each monitoring device may be installed in an active portion of the system. For example, in a water-based fire sprinkler system, each corrosion monitoring device may be installed in the flow path between the water source for the system and one or more sprinkler heads.

Figure 4:
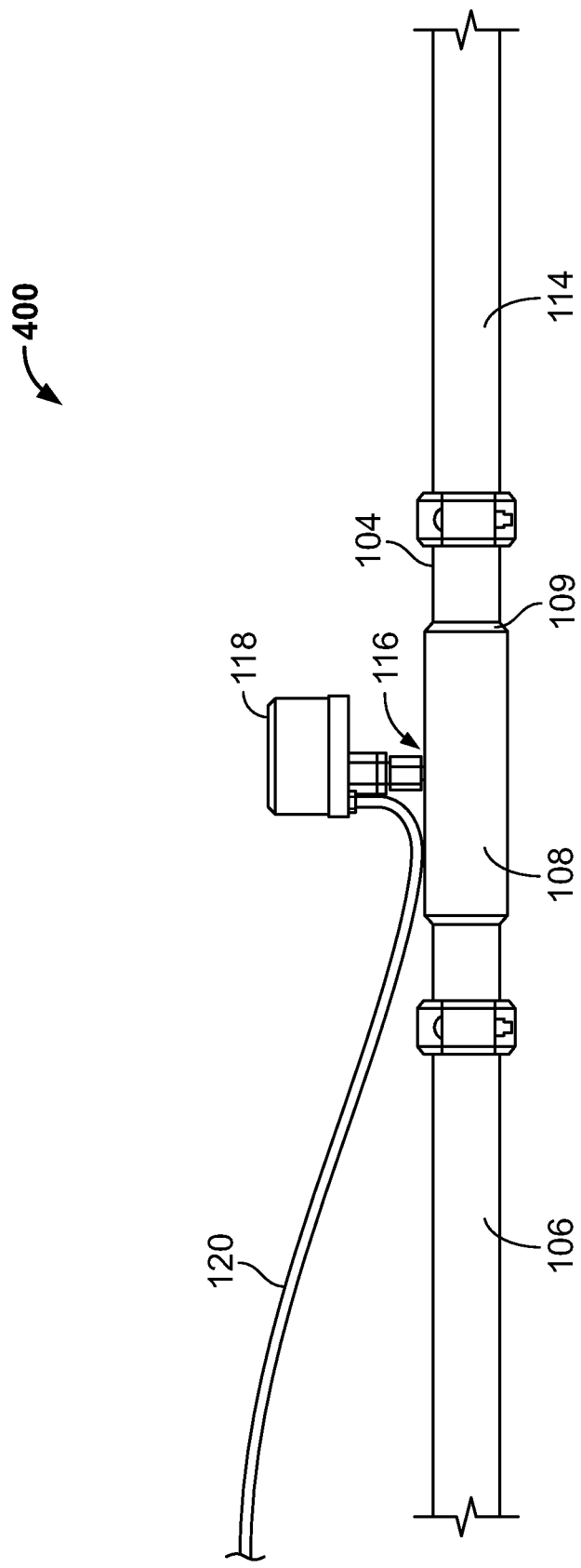
FIG. 4 is a side view of a corrosion monitoring assembly having a pressure assembly and signal conductor according to another example embodiment.

According to another example embodiment, FIG. 4 illustrates a corrosion monitoring assembly 400 having a first pipe portion 104 coupled between a second pipe portion 106 and a third pipe portion 114. A sleeve 108 is attached to the first pipe portion 104 via welds 109 to create a sealed chamber (not shown). A pressure assembly 118 is coupled to the sleeve 108 via port 116 of the sleeve 108. The pressure assembly 118 may include a pressure switch, pressure transducer, etc., for detecting a pressure inside the sealed chamber. A signal conductor 120 outputs a signal from the pressure assembly 118. The signal conductor may be a wire and may be coupled to a local indicator, a fire alarm panel, a building management system, monitoring station, etc. Alternatively, or in addition, the pressure assembly 118 may output signals wirelessly. The pressure assembly 118 may continuously output a signal corresponding to the pressure level inside the sealed chamber. Alternatively, or in addition, the pressure assembly 118 may output a signal when a change in pressure (or another parameter of interest) occurs.

Figure 5:
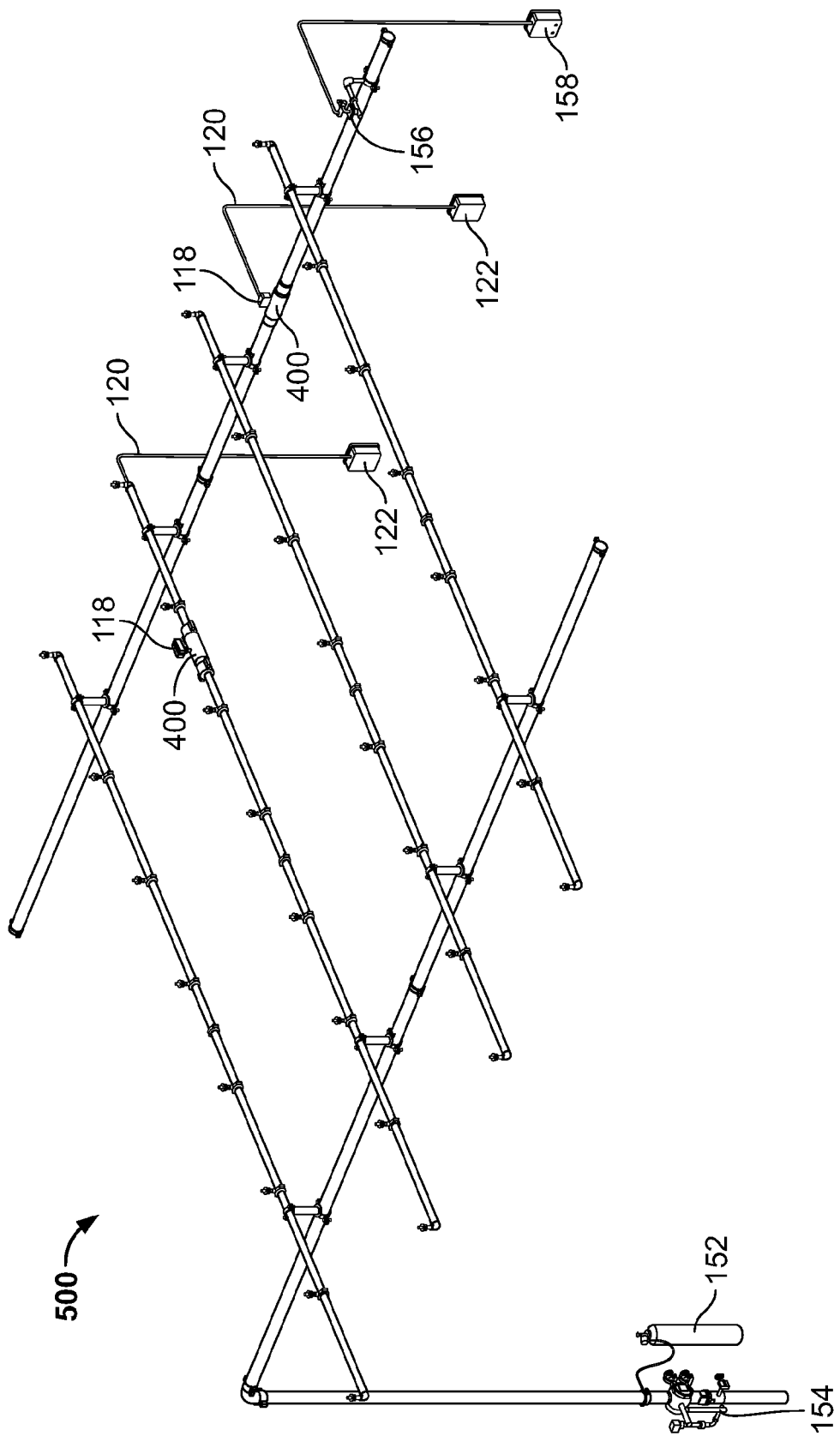
FIG. 5 is a perspective view of a wet pipe sprinkler system having a corrosion monitoring assembly according to another example embodiment of this disclosure.

FIG. 5 illustrates two corrosion monitoring assemblies 400 of FIG. 4 in an example wet pipe fire sprinkler system 500. As shown in FIG. 5, the wet pipe fire sprinkler system includes a source of gas 152 (e.g., a nitrogen gas cylinder) coupled to the piping network near a water valve 154 on a riser of the fire sprinkler system 500. A wet pipe vent 156 is coupled to the piping network to allow gas but not water to escape the piping network. The wet pipe vent 156 is connected to a vent indicator 158 to indicate a gas concentration within the piping network (e.g., a level of nitrogen gas in the piping network). A pressure assembly 118 of each corrosion monitoring assembly 400 is connected to a local indicator 122 (alternatively, or in addition to, a fire alarm panel, building management system, monitoring station, etc.) via a signal conductor 120 (e.g., an electrical conductor). Although two corrosion monitoring assemblies 400 are included in example fire sprinkler system 500, it should be understood that more or less corrosion monitoring assemblies may be included in other embodiments.

Figure 6:
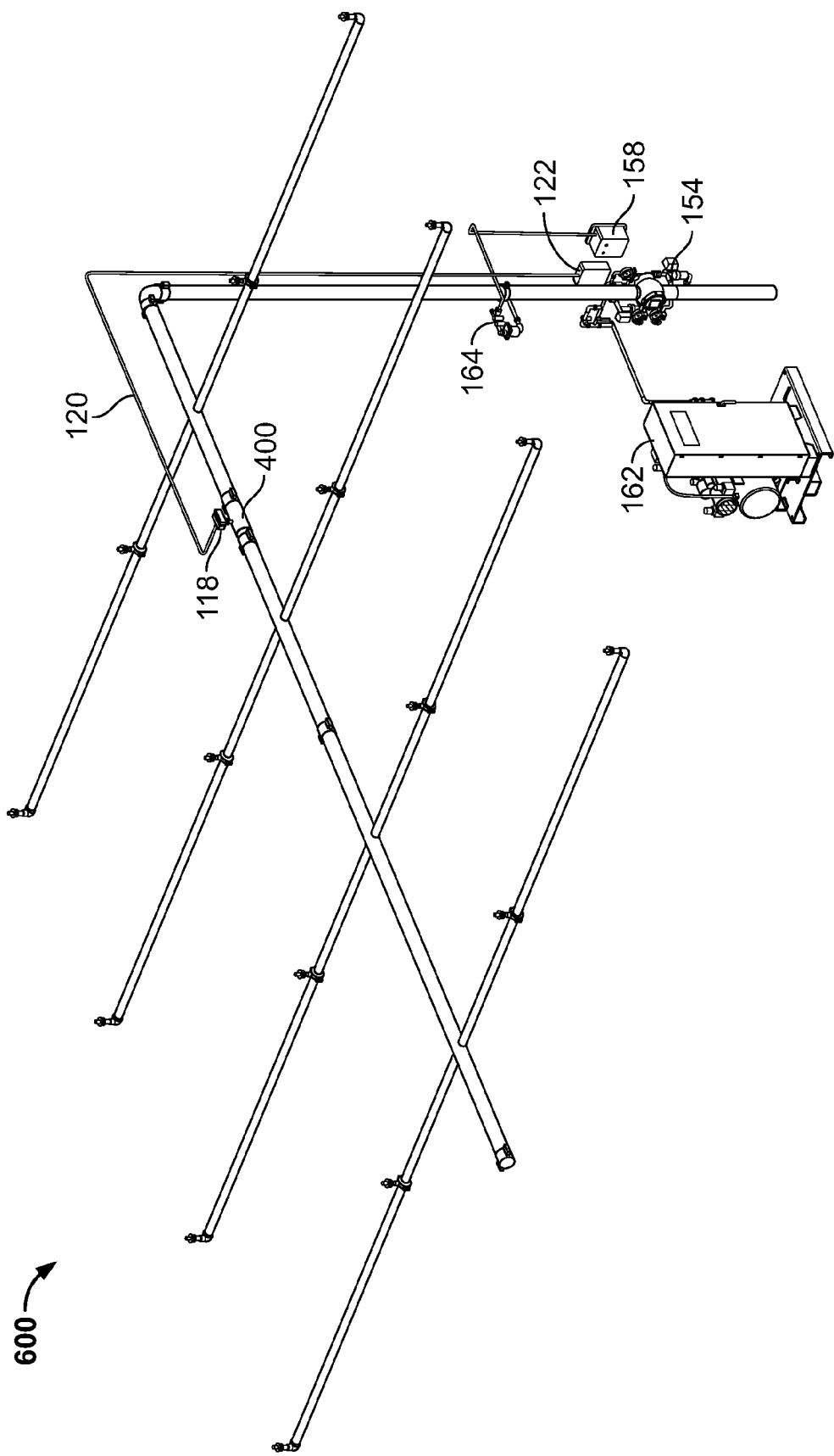
FIG. 6 is a perspective view of a dry pipe sprinkler system having a corrosion monitoring assembly according to another example embodiment.

FIG. 6 illustrates the corrosion monitoring assembly 400 of FIG. 4 in an example dry pipe fire sprinkler system 600. As shown in FIG. 6, the dry pipe fire sprinkler system 600 includes a generator 162 (e.g., a nitrogen generator) to provide pressurized gas to the piping network, near a water valve 154 on a riser of the fire sprinkler system 600. A dry pipe vent 164 is coupled to the piping network near the water valve 154 on the riser to allow gas but not water to escape the piping network. The dry pipe vent 164 is coupled to a vent indicator 158 to indicate a gas concentration within the piping network (e.g., a level of nitrogen gas in the piping network). A pressure assembly 118 of the corrosion monitoring assembly 400 is coupled to a local indicator 122 (alternatively, or in addition to, a fire alarm panel, building management system, monitoring station, etc.) via signal conductor 120. Although only one corrosion monitoring assembly 400 is included in the fire sprinkler system 600, it should be understood that multiple corrosion monitoring assemblies may be coupled to the dry pipe fire sprinkler system 600 to detect corrosion at multiple locations in the fire sprinkler system.

Further, the various corrosion monitoring devices described herein may include one or more audible indicators (e.g., buzzers) and/or one or more visual indicators (e.g., indicator lights) to provide alerts when a sensor detects a breach in the sealed chamber (i.e., instead of or in addition to sending a signal to a fire alarm panel, a building management system and/or a corrosion monitoring station as described above). Additionally, a test button may be included that, when activated, illuminates the visual indicator(s) and/or sounds the audible indicator(s) to verify the integrity and/or proper operation of the indicator(s), the overall assembly and/or the power source(s). The corrosion monitoring devices may also be adapted to provide a visual and/or audible indication (such as a flashing light or beeping sound) when an internal power source (e.g., a battery) requires service or replacement, when external power is removed, etc.

Figure 7:
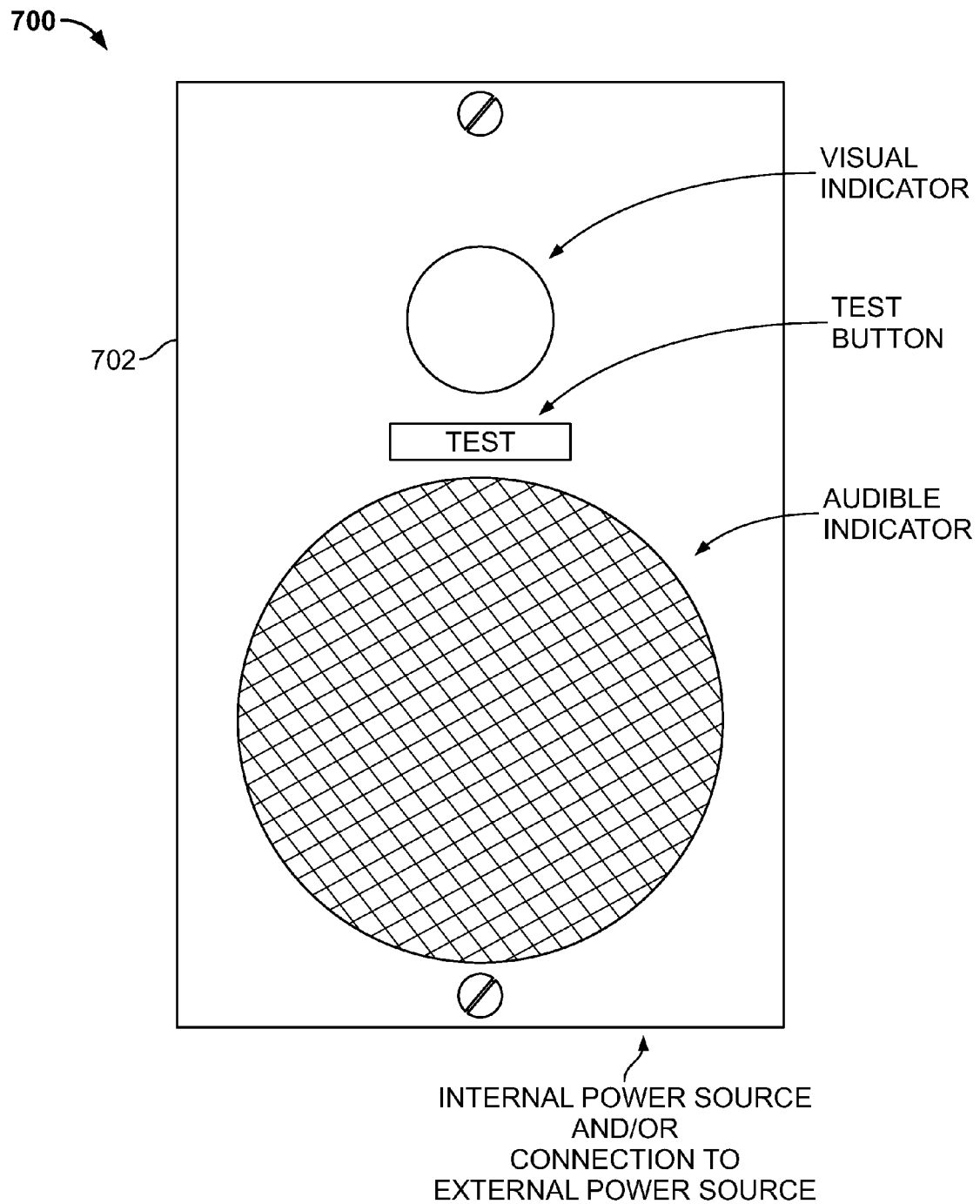
FIG. 7 is a front view of an annunciation device according to another aspect of the present disclosure.

FIG. 7 illustrates an example annunciation device 700 that includes a visual indicator, an audible indicator and a test button. The device 700 may be directly coupled to a corrosion monitoring device (e.g., via electric cable, pressure tubing, etc.). Alternatively, or in addition, the device 700 may be coupled to a fire alarm panel, a building management system and/or a remote corrosion monitoring station for receiving signals indicating the sensor detected a breach and, in response, activating the audible and/or visual indicators. The device 700 may include an internal power source (e.g., a lithium ion battery pack) and/or may be coupled to an external power source (e.g., utility power). The internal circuitry (not shown) may be configured such that no power is consumed until the sensor detects a breach. In the particular example shown in FIG. 7, the annunciation device 700 includes a housing 702 that may be mounted to its associated corrosion monitoring device or elsewhere, such as to a beam, wall or joist. The annunciation device 700 may also be adapted for mounting to a ceiling (e.g., to a ceiling tile) or other architectural or structural feature that may obstruct a direct line of sight from the floor (or other vantage point of an inspector) to the corrosion monitoring device, so the annunciation device is visible from the inspector's vantage point even if the corrosion monitoring device is not.

Each corrosion monitoring device may have a constant inner diameter that is the same as the system piping to which the monitoring device is coupled, as shown in FIG. 1. Alternatively, a corrosion monitoring device may have an inner diameter that is less than, or greater than, the inner diameter of the adjoining system piping.

Figure 8:
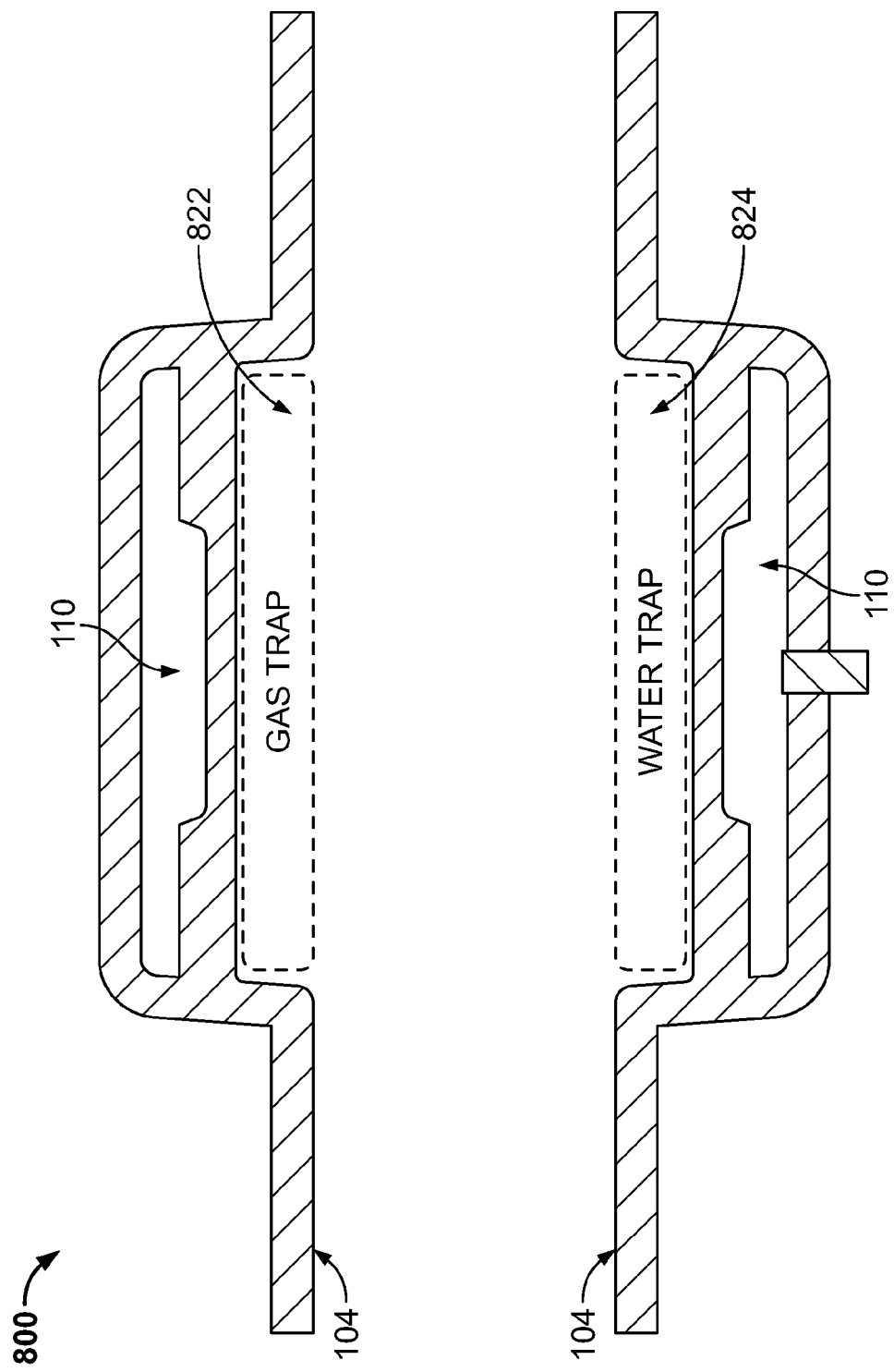
FIG. 8 is a side cross-section view of a corrosion monitoring assembly having optional gas and water traps according to another aspect of the present disclosure.

FIG. 8 illustrates a corrosion monitoring device 800 having a center section with an inner diameter that is greater than the inner diameter of the adjacent system piping 104. As a result, the device 800 includes an artificial low point that functions as a "water trap" 824 above a portion of the sealed chamber 110, as well as an artificial high point that functions as a "gas trap" 822 below a portion of the sealed chamber 110. Because the device 800 is designed to trap water and gas, the device 800 may experience more corrosion than other piping in the system, regardless of where the device 800 is located in the fire sprinkler system. The device 800 is well suited for dry pipe sprinkler systems and wet pipe sprinkler systems. In dry pipe sprinkler systems, the water trap may collect any residual water in the system and therefore represent the mostly likely site of corrosion (i.e., around the six o'clock position). In wet pipe sprinkler systems, the gas trap may collect any gas (including oxygen) in the system and therefore represent the mostly likely site of corrosion (i.e., around the twelve o'clock position). In other embodiments, the corrosion monitoring device may be provided with a water trap or an air trap (but not both).

Figure 9:
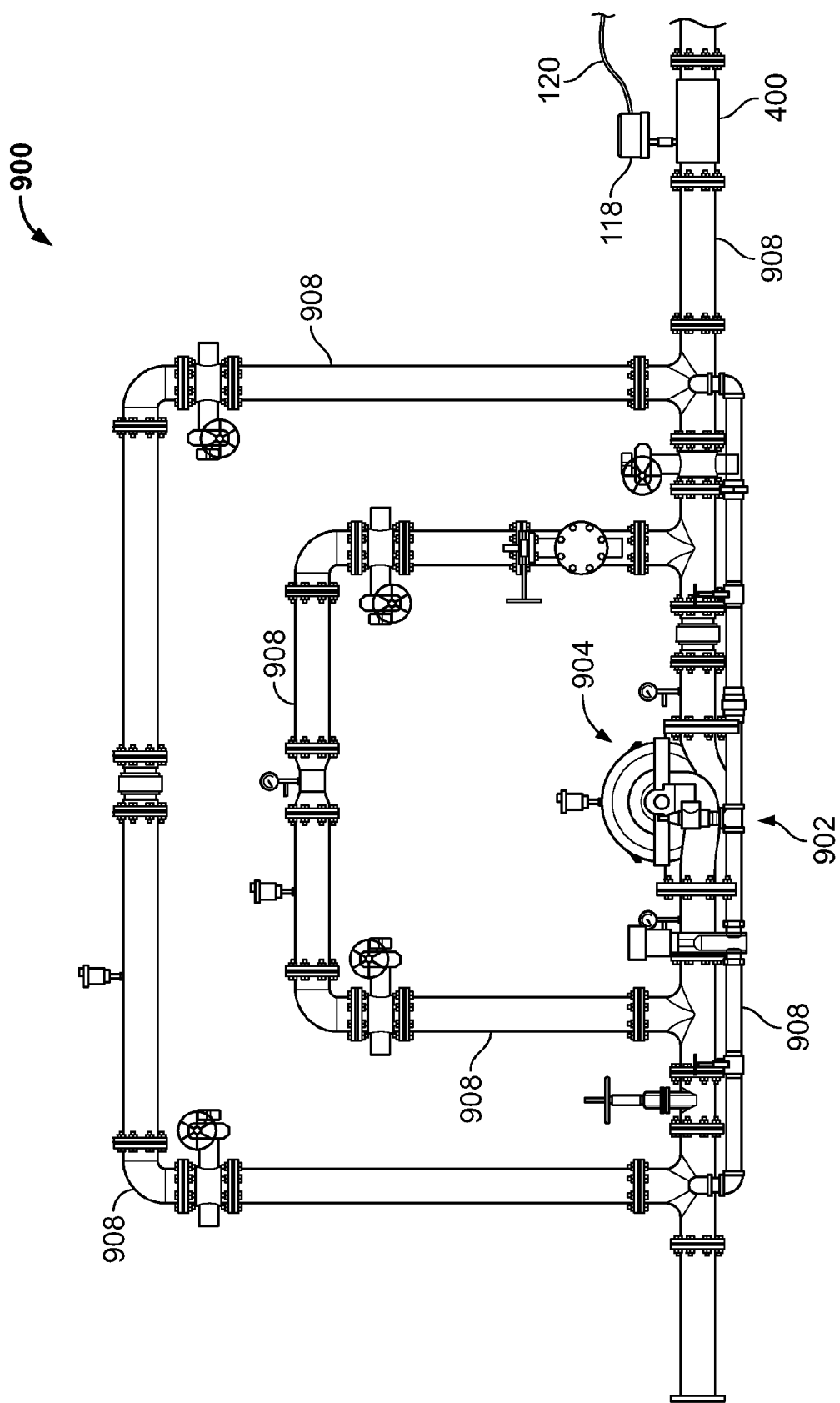
FIG. 9 is a side view of a water supply system including a corrosion monitoring assembly.

FIG. 9 illustrates an example water supply system 900 including a pump assembly 902, pipes 908, and a corrosion monitoring assembly 400 coupled to the water supply system 900. The pump assembly 902 includes a water pump 904. The corrosion monitoring assembly 400 is coupled to the pipes 908 of the water supply system 900 and may be configured to monitor corrosion at a point where water exits the pump assembly 902. The corrosion monitoring assembly 400 includes a pressure assembly 118, which may output signals to a local indicator, fire alarm panel, building management system, monitoring station, etc., via signal conductor 120.

According to another aspect of the present disclosure, a method of monitoring corrosion within a fire sprinkler system having a pipe, and structure coupled to the pipe and defining a sealed chamber between the structure and the pipe, is disclosed. The method includes sensing (e.g., using a suitable sensor such as a pressure sensor, conductance probe, temperature sensor, etc.) a parameter associated with the sealed chamber (e.g., a pressure within the sealed chamber, an absence or presence of a liquid, temperature, etc.). The method also includes detecting a change in the parameter associated with the sealed chamber (e.g., a change in pressure), corresponding to a breach of a pipe wall of the sealed chamber. The method further includes generating a signal in response to detecting the change in the parameter. The signal may be indicative of the change in the parameter (e.g., magnitude of the change, direction of the change, etc.). The signal may optionally be transmitted to a local indicator, a fire alarm panel, a building management system, monitoring station, etc.

After a sensor detects a breach in the sealed chamber of a corrosion monitoring assembly, the assembly may be evaluated (in situ or following removal from the system) to determine the cause and/or extent of the corrosive attack. This may include identifying the type(s) of pits formed in the assembly and/or the pit depth, density, distribution, etc. Corrective action may be recommended for and/or performed on the system, possibly including coupling a nitrogen source to the system, replacing a nitrogen source (such as a faulty nitrogen generator), removing oxygen from the system (using vents, nitrogen and/or other means), draining and/or filling the system, replacing one or more pipes in the network, installing one or more corrosion monitoring devices in the system, etc., and providing instructions for one or more of these actions. The assembly may be easily replaced by another assembly after a breach occurs.

Although the example embodiments described above are specific to water-based fire sprinkler systems, it should be understood that the teachings of the present disclosure are applicable to any pipe system, including pressurizable and non-pressurized pipe systems, and are therefore not limited to fire sprinkler systems.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A water-based fire sprinkler system comprising:
   a water source;
   one or more sprinkler heads;
   a corrosion monitoring device positioned in a flow path between the water source and the one or more sprinkler heads, the corrosion monitoring device including a first pipe having opposite ends and a middle portion including a wall having a first wall thickness, a structure coupled to the first pipe and defining a sealed chamber between said wall of the middle portion and the structure, and a sensor to sense a pressure in the sealed chamber or a presence of liquid in the sealed chamber, the opposite ends of the first pipe each including a wall having a second wall thickness; and
   a second and a third pipe coupled to the opposite ends of the first pipe, the second and third pipes each including a wall having the second wall thickness;
   wherein the second wall thickness is greater than the first wall thickness;
   wherein the first, second and third pipes are each rigid pipes comprising black iron or galvanized steel;
   wherein a change in the pressure in the sealed chamber or the presence of liquid in the sealed chamber corresponds to a breach of said wall of the middle portion due to corrosion and is indicative of corrosion damage in the second and third pipes of the water-based fire sprinkler system.

2. The system of claim 1, wherein the opposite ends of the first pipe each have an outer diameter, and wherein the structure includes a sleeve having an inner diameter greater than the outer diameter.

3. The system of claim 2, wherein the first pipe includes a wall that transitions from the first wall thickness to the second wall thickness adjacent opposite ends of the first pipe to define tapered shoulders between the middle portion and the opposite ends of the first pipe.

4. The system of claim 1, wherein the second and third pipes are coupled to the opposite ends of the first pipe via at least one of a roll grooved coupling, a cut grooved coupling, a threaded coupling and weld(s).

5. The system of claim 1, wherein the corrosion monitoring device includes a water trap positioned above a portion of the sealed chamber.

6. The system of claim 1, wherein the sealed chamber is positioned between the structure and at least a top side of the first pipe.

7. The system of claim 1, wherein the sensor is connected via a wired and/or wireless communication channel to a building management system.

8. The system of claim 1, wherein the sensor is connected via a wired and/or wireless communication channel to a corrosion monitoring station.

9. The system of claim 1, wherein the sealed chamber extends around a circumference of the first pipe.

10. The system of claim 1, wherein the structure is coupled to the first pipe via welds.

11. The system of claim 1, wherein the sensor is configured to produce at least one of an analog and a digital signal representing a pressure or a change in pressure in the sealed chamber.

12. The system of claim 11, wherein the sensor includes a pressure transducer.

13. The system of claim 11, wherein the sensor includes pressure tubing.

14. The system of claim 11, wherein the sensor includes a pressure switch.

15. The system of claim 1, wherein the sensor is connected via at least one of a wired and a wireless communication channel to a fire alarm panel.

16. The system of claim 1, wherein the sealed chamber is positioned between the structure and at least a bottom side of the first pipe.

17. The system of claim 1, wherein the structure includes a port extending to the sealed chamber, and wherein the sensor includes a pressure tubing connector coupled to the port and pressure tubing coupled to the pressure tubing connector.

18. The system of claim 1, wherein the fire sprinkler system is a wet pipe system.

19. The system of claim 1, wherein the fire sprinkler system is a dry pipe system.

20. The system of claim 1, wherein the corrosion monitoring device includes a gas trap positioned below a portion of the sealed chamber.

21. The system of claim 1, wherein the sensor includes a liquid sensor configured to sense a presence of liquid in the sealed chamber.

22. The system of claim 1, wherein the sensor includes a conductance probe.

* * * * *